(12) United States Patent
Burke et al.

(10) Patent No.: US 11,980,535 B2
(45) Date of Patent: May 14, 2024

(54) METHOD OF USING A CARDIOVASCULAR GRAFT TO REDUCE THROMBOSIS OR PLATELET ADHESION

(71) Applicant: Xeltis, A.G., Zurich (CH)

(72) Inventors: Luke David Burke, Eindhoven (NL); Martijn Antonius Johannes Cox, Budel (NL); Aurelie Serrero, 's-Hertogenbosch (NL)

(73) Assignee: Xeltis AG, Zurich (CH)

( * ) Notice: Subject to any disclaimer, the term of this patent is extended or adjusted under 35 U.S.C. 154(b) by 226 days.

(21) Appl. No.: 17/183,543

(22) Filed: Feb. 24, 2021

(65) Prior Publication Data
US 2021/0177567 A1   Jun. 17, 2021

Related U.S. Application Data

(63) Continuation of application No. 15/940,037, filed on Jun. 12, 2018, now abandoned.
(Continued)

(51) Int. Cl.
*A61F 2/06* (2013.01)
*A61F 2/00* (2006.01)
(Continued)

(52) U.S. Cl.
CPC .............. *A61F 2/0077* (2013.01); *A61F 2/06* (2013.01); *A61L 27/18* (2013.01); *A61L 31/04* (2013.01); *A61L 31/14* (2013.01); *A61L 31/146* (2013.01); *A61L 31/148* (2013.01); *A61L 31/16* (2013.01); *A61L 33/0005* (2013.01);
(Continued)

(58) Field of Classification Search
CPC ....... A61M 1/3655; A61F 2/0077; A61F 2/06; A61F 2002/091; A61F 2002/081; A61F 2210/0004; A61F 2240/001; A61F 2250/0067; A61L 27/18; A61L 31/04; A61L 31/14; A61L 31/146; A61L 31/148;
(Continued)

(56) References Cited

U.S. PATENT DOCUMENTS

| | | | |
|---|---|---|---|
| 2002/0019402 A1* | 2/2002 | Dominguez | A61P 17/02 560/24 |
| 2003/0044418 A1* | 3/2003 | Davis | A61P 9/10 424/184.1 |

(Continued)

FOREIGN PATENT DOCUMENTS

WO   WO-2016120456 A1 *  8/2016  ............. A61L 27/26

OTHER PUBLICATIONS

Atar et al. Synergism of Aspirin and Heparin with a Low-Frequency Non-Invasive Ultrasound System for Augmentation of In-Vitro clot Lysis. J Thrombisis 15(3) 165-169, 2003.
(Continued)

*Primary Examiner* — Paul B Prebilic
(74) *Attorney, Agent, or Firm* — LUMEN PATENT FIRM

(57) ABSTRACT

A cardiovascular graft is provided with highly reduced thrombogenicity. The cardiovascular graft is an electrospun non-woven mesh produced from supramolecular polymers with large diameter fibers. The cardiovascular graft can be implemented as a vascular graft into the human body to allow vascular bypass/reconstruction, or repeated venous access for dialysis treatment, as well as other disorders of small-diameter blood vessels.

13 Claims, 13 Drawing Sheets

Related U.S. Application Data

(60) Provisional application No. 62/611,431, filed on Dec. 28, 2017, provisional application No. 62/479,554, filed on Mar. 31, 2017.

(51) Int. Cl.

| | | |
|---|---|---|
| *A61L 27/18* | (2006.01) | |
| *A61L 31/04* | (2006.01) | |
| *A61L 31/14* | (2006.01) | |
| *A61L 31/16* | (2006.01) | |
| *A61L 33/00* | (2006.01) | |
| *A61L 33/06* | (2006.01) | |
| *A61M 1/36* | (2006.01) | |

(52) U.S. Cl.
CPC ......... *A61L 33/0047* (2013.01); *A61L 33/007* (2013.01); *A61L 33/06* (2013.01); *A61M 1/3655* (2013.01); *A61F 2002/0081* (2013.01); *A61F 2002/0091* (2015.04); *A61F 2210/0004* (2013.01); *A61F 2240/001* (2013.01); *A61F 2250/0067* (2013.01); *A61L 2300/42* (2013.01); *A61L 2300/432* (2013.01)

(58) Field of Classification Search
CPC . A61L 31/16; A61L 2300/42; A61L 2300/432
See application file for complete search history.

(56) References Cited

U.S. PATENT DOCUMENTS

| | | | |
|---|---|---|---|
| 2015/0057237 A1* | 2/2015 | Dankers | C08G 18/672 |
| | | | 514/56 |
| 2015/0173921 A1* | 6/2015 | Lavrijsen | A61L 27/18 |
| | | | 623/23.72 |
| 2018/0015202 A1* | 1/2018 | Dankers | A61L 33/062 |
| 2018/0274131 A1* | 9/2018 | Naz | D01D 5/0084 |
| 2019/0201588 A1* | 7/2019 | Serrero | D01F 6/78 |
| 2021/0177567 A1* | 6/2021 | Burke | A61L 31/146 |

OTHER PUBLICATIONS

Neuman et al. Augmentation of in-stent clot dissolution by low frequency ultrasound combined with aspirin and heparin. An ex-vivo canine shunt study. Thrombosis Research 112 (2003) 99-104.

Sabatine et al. Combination of a Direct Thrombin Inhibitor and a Platelet Glycoprotein IIb/IIIa Blocking Peptie Facilitates and Maintains Reperfusion of Platalet-Rich Thrombus with Alteplase. J. Thrombosis and Thrombolysis 10, 189-196, 2000.

* cited by examiner

METHOD OF USING A CARDIOVASCULAR GRAFT TO REDUCE THROMBOSIS OR PLATELET ADHESION

CROSS-REFERENCE TO RELATED APPLICATIONS

This application is a continuation of U.S. patent application Ser. No. 15/940,037 filed Mar. 29, 2018, which is incorporated herein by reference. U.S. patent application Ser. No. 15/94,003 claims priority from U.S. Provisional Patent Application 62/479,554 filed Mar. 31, 2017, which is incorporated herein by reference. This application claims priority from U.S. Provisional Patent Application 62/611,431 filed Dec. 28, 2017, which is incorporated herein by reference.

FIELD OF THE INVENTION

This invention relates to electrospun coatings, grafts or materials to inhibit thrombogenic effects.

BACKGROUND OF THE INVENTION

Vascular disease involving blood vessels with a luminal diameter of 6 mm or less constitutes the majority of disease cases requiring clinical intervention. In many of these cases the preferred intervention is vascular reconstruction or bypass surgery, utilizing either autologous vessels harvested from elsewhere in the patient or synthetic vascular grafts. Such synthetic grafts are available in a range of dimensions and configurations and generally have a small set of medical polymers such as poly(tetrafluoroethylene) (PTFE) and Poly(etherterephthalate)(PET) in either woven or dendritic assemblies.

The predominantly observed failure mode of synthetic vascular grafts in clinical setting is progressive intimal hyperplasia at venous (outflow) anastomosis leading to reduced flow and thrombosis of the graft. This is thought to be caused by perturbations to flow resulting from the connection between the graft and the native vessel, the disparities between mechanical properties (such as compliance) of the graft material and the native tissue, as well as the foreign-body thrombogenic nature of the graft material in contact with circulating blood. However, the precise mechanisms for thrombosis remain a major focus of current research efforts in the field.

Hemostasis encompasses the myriad of biological processes by which bleeding from damaged tissues or blood vessels is stopped. A primary mechanism of hemostasis is the activation and adhesion of circulating thrombocytes, also known as platelets. Within seconds of injury to tissue, released proteins cause platelets to "activate", expressing adhesive structures at their surface and allowing them to bind to the injury site and begin to form a "plug" to prevent further blood loss. In addition, activated platelets release further chemical signals to recruit and activate further circulating platelets in a cascade effect, these platelets may bind either to the injury site or to other activated platelets.

An intravascular thrombus results from a pathological disturbance of the hemostasis process. Often, platelet activation, adhesion and aggregation occur within a vessel due to turbulent flow, interactions between foreign materials and circulating platelets, release of signaling proteins from damaged vessel walls, or others. As these platelets are activated and, in turn, activate further circulating platelets, which adhere to the growing thrombus, an occlusion of the vessel occurs, limiting or completely preventing blood flow. These conditions are exacerbated in vessels with low volumetric flow rates, typically below 600 mL/min. This is due to circulating platelets remaining in the vicinity of the growing thrombus for a longer time, as well as reduced shear stresses on adhered platelets due to reduced flow, reducing the potential for activated platelets to be removed.

The present invention advances the art by providing vascular grafts with highly reduced thrombogenicity.

SUMMARY OF THE INVENTION

A cardiovascular graft to reduce thrombogenic effects is provided for applications like a coronary bypass graft or an arteriovenous graft for dialysis access. The cardiovascular graft has a tubular structure with an inner wall made out of a fibrous network of supramolecular compounds having hard-blocks covalently bonded with soft-blocks. The hard-blocks has 2-ureido-4[1H]-pyrimidinone (UPy) compounds. The hard-blocks could further include chain extenders at a range of 1 to 5, or even more preferred 1.5 to 3, for the chain extenders over the UPy compounds. The soft-blocks are a biodegradable polyester, polyurethane, polycarbonate, poly(ortho)ester, polyphosphoester, polyanhydride, polyphosphazene, polyhydroxyalkanoate, polyvinylalcohol, polypropylenefumarate or any combination thereof. The molecular weight of the soft-block ranges between 500 and 3000 Da.

The fibrous network is a bioresorbable electrospun nonwoven fibrous network with fibers having an average fiber diameter of 1-10 microns. The tubular structure has an inner diameter between 2-8 mm, and a wall thickness of 200-900 microns.

In one variation of the embodiment, the inner wall has a thickness of at least 20 micrometers and pores with an average pore size between 5 and 10 micrometers.

In another variation of the embodiment, the inner wall has pores with an average pore size between 5 and 8 micrometers and an average porosity ranging from 50 to 80%.

In yet another variation of the embodiment, the tubular structure has an inner diameter between 3-6 mm and a wall thickness of 200-800 microns.

In still another variation of the embodiment, the tubular structure has an inner diameter between 4-8 mm and a wall thickness of 300-900 microns.

In still another variation of the embodiment, the tubular structure has an inner diameter of 5 mm or less.

In still another variation of the embodiment, the fibers having an average fiber diameter of 4-8 microns.

In still another variation of the embodiment, the fibers having an average fiber diameter of 4-6 microns.

In still another variation of the embodiment, the inner layer of the graft is hydrophobic, with a water contact angle of between 110 and 140 degrees.

In still another variation of the embodiment, the tubular structure has an outer wall reinforced by a braided structure, polymer strands, compounds or a combination thereof to provide resistance to prevent collapse of the cardiovascular graft.

In still another variation of the embodiment, the cardiovascular graft could include an $\alpha_{IIb}\beta_3$ inhibitor.

In still another variation of the embodiment, the cardiovascular graft could be provided in combination with oral, intravenous or other administration of an $\alpha_{IIb}\beta_3$ inhibitor.

BRIEF DESCRIPTION OF THE DRAWINGS

FIG. 1A shows high magnification view of platelet adhesion and spreading behavior on SP electrospun fibres with average diameter of 4-6 μm. FIG. 1B shows high magnification view of platelet adhesion and spreading behavior on SP electrospun fibres with average diameter of <1 μm. FIG. 1C shows high magnification view of platelet adhesion and spreading behavior on non-woven PTFE fibers with average diameter of <1 μm.

FIG. 2A shows low magnification view of platelet spreading behavior on SP electrospun fibers with average diameter of 4-6 μm FIG. 2B shows low magnification view of platelet spreading behavior on SP electrospun fibers with average diameter of <1 μm, and FIG. 2C shows low magnification view of platelet spreading behavior on non-woven PTFE fibers with average diameter of <1 μm.

(FIG. 3A) Original SEM image (FIG. 3B) Cropped, enhanced contrast image from "FIG. 3A" (FIG. 3C) Binary image generated from "FIG. 3B" (FIG. 3B) ImageJ automated thresholding to result in absolute black/white pixels from "FIG. 3C" showing a 27.35% total porosity.

DETAILED DESCRIPTION

Figure 1A:
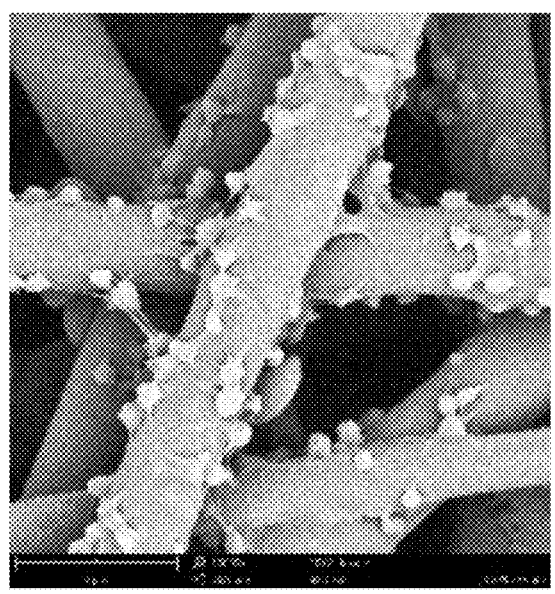
FIGS. 1A-C show according to an exemplary embodiment of the invention SEM images (10,000× times magnification) of platelet adherence and activation on supramolecular polymer (SP) micron and submicron electrospun fibers as compared to PTFE nonwovens.
Figure 1B:
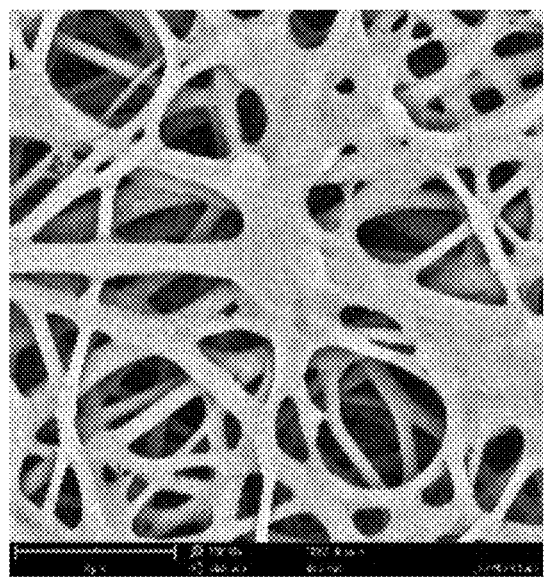
Figure 1C:
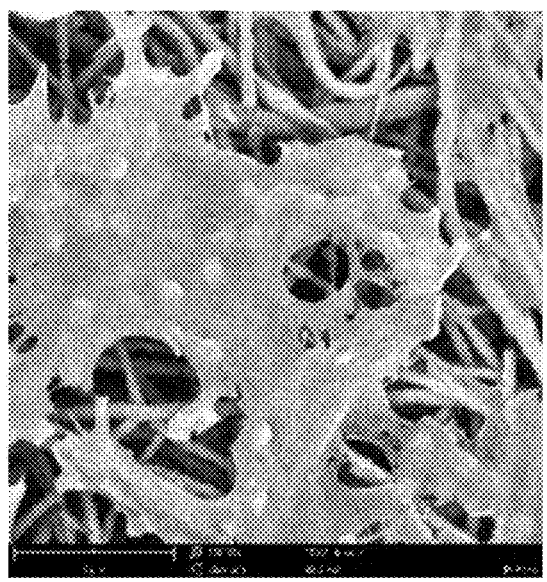
Figure 2A:
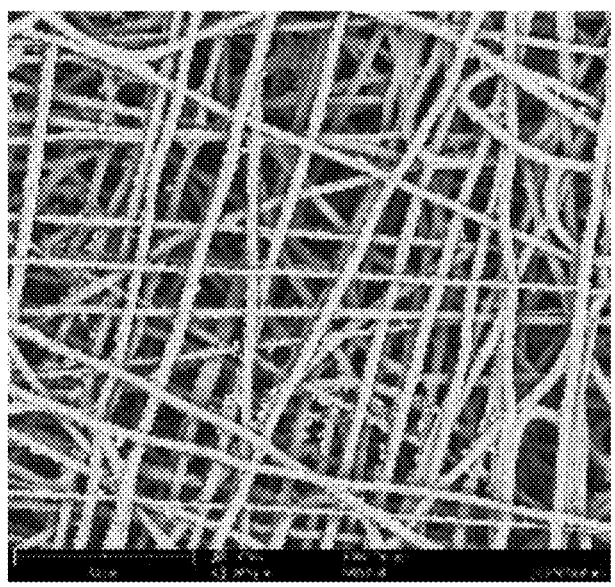
FIGS. 2A-C show according to an exemplary embodiment of the invention platelet spreading on SP micron-and submicron-fibers as compared to PTFE nonwovens
Figure 2B:
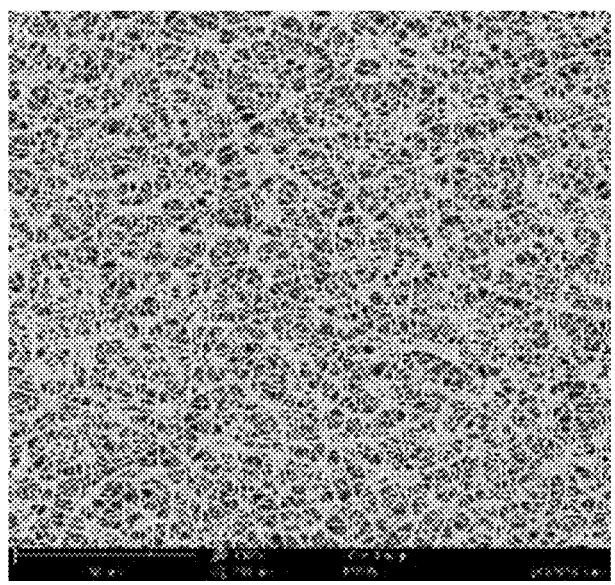
Figure 2C:
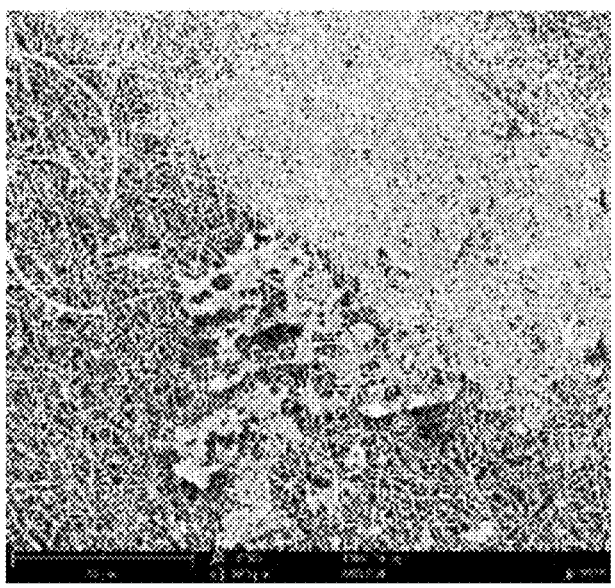

The invention relates to a cardiovascular graft with highly reduced thrombogenicity by having an electrospun mesh produced from supramolecular polymers (SP). Preferably, the vascular graft is a non-woven mesh and/or large diameter fibers. The invention also relates to a method to produce such grafts via electrospinning. The invention further relates to the implantation of the vascular graft into the human body to allow vascular bypass/reconstruction, or repeated venous access for dialysis treatment, as well as other disorders of small-diameter blood vessels.

With the design of the cardiovascular graft, as defined infra, the inventors have demonstrated and describe herein unexpected platelet behavior on vascular grafts produced from SP. Platelet activation and adhesion were observed without significant spreading, aggregation or philopodia formation, in stark contrast with widely available "biocompatible" materials such as PTFE. Such outcomes prove that the material is ideal for small-diameter grafts where thrombosis and/or stenosis is a key concern. Moreover, the employed SP materials are bioabsorbable, and enable tissue infiltration and regrowth. This ensures that the risk of long-term remodeling, neo-intima formation and ongoing inflammatory response leading to stenosis of the vessel is greatly mitigated.

Definition of Cardiovascular Graft to Inhibit Thrombogenic Effects

The cardiovascular graft to reduce thrombogenic effects is defined by a tubular structure with an inner wall made out of a fibrous network of supramolecular compounds having hard-blocks covalently bonded with soft-blocks. The hard-blocks comprise 2-ureido-4[1H]-pyrimidinone (UPy) compounds. The fibrous network is a bioresorbable electrospun non-woven fibrous network with fibers having an average fiber diameter of 1-10 microns. The tubular structure has an inner diameter between 2-8 mm, and a wall thickness of 200-900 microns.

Variations to the cardiovascular graft can be defined by the following structural aspects, either individually or in any combination, if applicable, thereof:

- An inner wall with a thickness of at least 20 micrometers and pores with an average pore size between 5 and 10 micrometers.
- An inner wall with pores having an average pore size between 5 and 8 micrometers and an average porosity ranging from 50 to 80%.
- A tubular structure with an inner diameter between 3-6 mm and a wall thickness of 200-800 microns.
- A tubular structure with an inner diameter between 4-8 mm and a wall thickness of 300-900 microns.
- A tubular structure with an inner diameter of 5 mm or less.
- Fibers with an average fiber diameter of 4-8 microns or an average fiber diameter of 4-6 microns.
- Soft-blocks comprising a biodegradable polyester, polyurethane, polycarbonate, poly(ortho)ester, polyphosphoester, polyanhydride, polyphosphazene, polyhydroxyalkanoate, polyvinylalcohol, polypropylenefumarate or any combination thereof.
- Soft-blocks with a molecular weight ranging between 500 and 3000 Da.

Hard-blocks comprising chain extenders at a range of 1 to 5, or even more preferred 1.5 to 3, for the chain extenders over the UPy compounds.

The inner layer of the graft is hydrophobic, with a water contact angle of between 110 and 140 degrees.

The cardiovascular graft is a coronary bypass graft or an arteriovenous graft for dialysis access.

The tubular structure has an outer wall reinforced by a braided structure, polymer strands, compounds or a combination thereof to provide resistance to prevent collapse of the cardiovascular graft.

The cardiovascular graft comprises an $\alpha_{IIb}\beta_3$ inhibitor, which pronounces the non-thrombogenic effect even more.

The cardiovascular graft is provided in combination with administration of an $\alpha_{IIb}\beta_3$ inhibitor, which pronounces the non-thrombogenic effect even more.

The supramolecular polymer (SP) referenced herein may comprise the ureido-pyrimidinone (UPy) quadruple hydrogen-bonding motif and a polymer backbone, for example selected from the group of biodegradable polyesters, polyurethanes, polycarbonates, poly(orthoesters), polyphosphoesters, polyanhydrides, polyphosphazenes, polyhydroxylkanoates, polyvinylalcohol, polypropylenefumarate. Examples of polyesters are polycaprolactone, poly(L-lactide), poly(DL-lactide), poly(valerolactone), polyglycolide, polydioxanone, and their copolyesters. Examples of polycarbonates are poly(trimethylenecarbonate), poly(dimethyltrimethylenecarbonate), poly(hexamethylene carbonate).

The same reduced adhesion of platelets may occur in conjunction with alternative, non-supramolecular polymers, if properties are carefully selected and material processed to ensure required surface characteristics. These polymers may be biodegradable or non-biodegradable polyesters, polyurethanes, polycarbonates, poly(orthoesters), polyphosphoesters, polyanhydrides, polyphosphazenes, polyhydroxylkanoates, polyvinylalcohol, polypropylenefumarate. Examples of polyesters are polycaprolactone, poly(L-lactide), poly(DL-lactide), poly(valerolactone), polyglycolide, polydioxanone, and their copolyesters. Examples of polycarbonates are poly(trimethylenecarbonate), poly(dimethyltrimethylenecarbonate), poly(hexamethylene carbonate).

In addition, the morphology of the graft's luminal surface plays an important role in thrombogenic properties. Experiments performed in vitro with human blood reveal that fiber diameter of the non-woven mesh is key, with larger diameter fibers of 4-6 µm being preferred over smaller fibers.

Platelet Aggregation on Scaffolds made from Supramolecular Polymer

Samples of electrospun SP materials with various surface morphologies were coated onto PET sheets coated with indium tin oxide (ITO). These samples were exposed via a constant-shear rate flow cell to a perfusion of human blood containing 3.2% citrate to inhibit thrombin activation, allowing platelet behaviour to be specifically investigated. After 30 minutes of perfusion the flow cell was removed and the surface of the material was fixed using ethanol dehydration and characterised via scanning electron microscopy (SEM). Negative controls were performed on bare PET-ITO sheet and showed no significant platelet adherence. Positive controls were performed on collagen-coated PET-ITO and showed significant platelet cluster formation. All experiments were performed in triplicate, with multiple healthy blood donors.

The electrospun SP meshes showed significantly reduced platelet activity as compared to market-available PTFE nonwoven materials. This effect was clearest on larger-diameter fibres, however reduced spreading was also apparent on submicron fibres, with morphology similar to PTFE nonwovens. SEM images of platelet adherence to the SP fibres and nonwoven PTFE are shown at high magnification (10,000×). Platelet adherence to fibres and activation is clearly observed, however aggregation and spreading of platelets is significantly reduced compared to PTFE nonwovens. Lower magnification (1000×) SEM images of all substrates are also shown, demonstrating the reduction in platelet spreading and aggregation over a greater area.

The UPy-based electrospun fibers show decreased platelet spreading and aggregation in human blood as compared to market available biocompatible materials with similar morphology. The observed platelet behaviour is unusual and highly relevant for bioabsorbable devices intending to achieve tissue remodelling. The presence of an activated platelet coating incites subsequent remodelling phases and re-epithelialization. However, the presence of an active platelet layer is frequently accompanied by a severe thrombogenic response, leading to rapid occlusion of small-diameter conduits comprised of synthetic materials. Therefore, the demonstrated platelet response represents an ideal situation for the formation of neo-tissues over a bioabsorbable substrate, which is theorized to result in a wholly non-thrombogenic biological surface. Furthermore, the nature of supramolecular chemistry allows a degree of flexibility in mechanical properties of synthesized polymers, allowing increased tunability of device properties to further improve blood response.

Figure 3A:
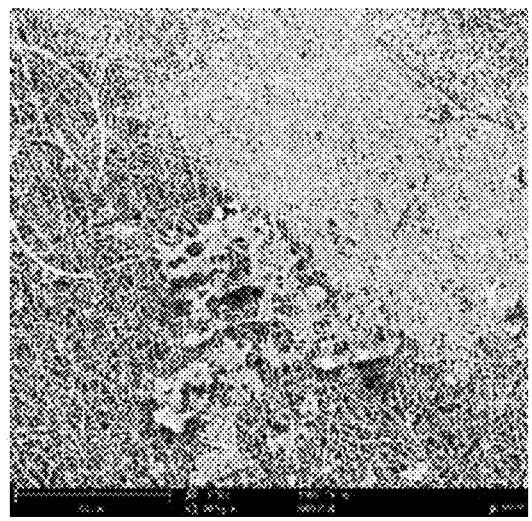
FIGS. 3A-C show according to an exemplary embodiment of the invention an analysis method of surface porosity in test materials after blood perfusion.
Figure 3B:
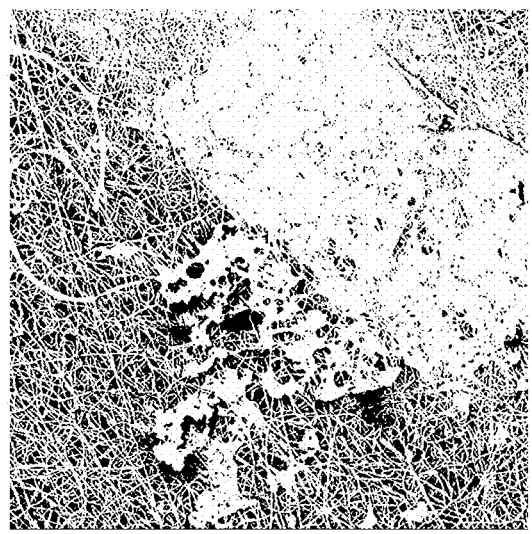
Figure 3C:
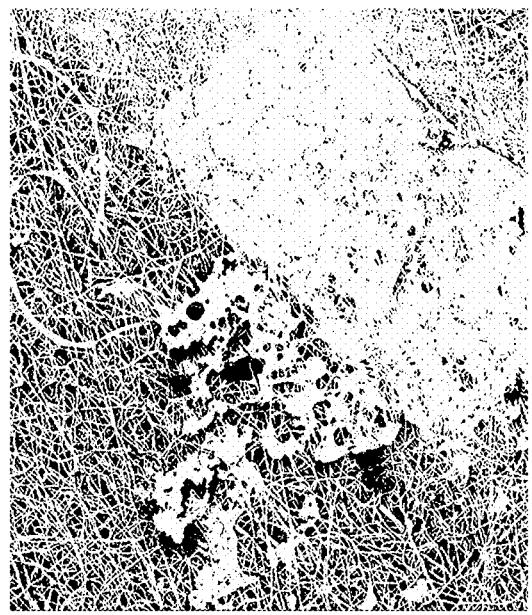
Figure 4:
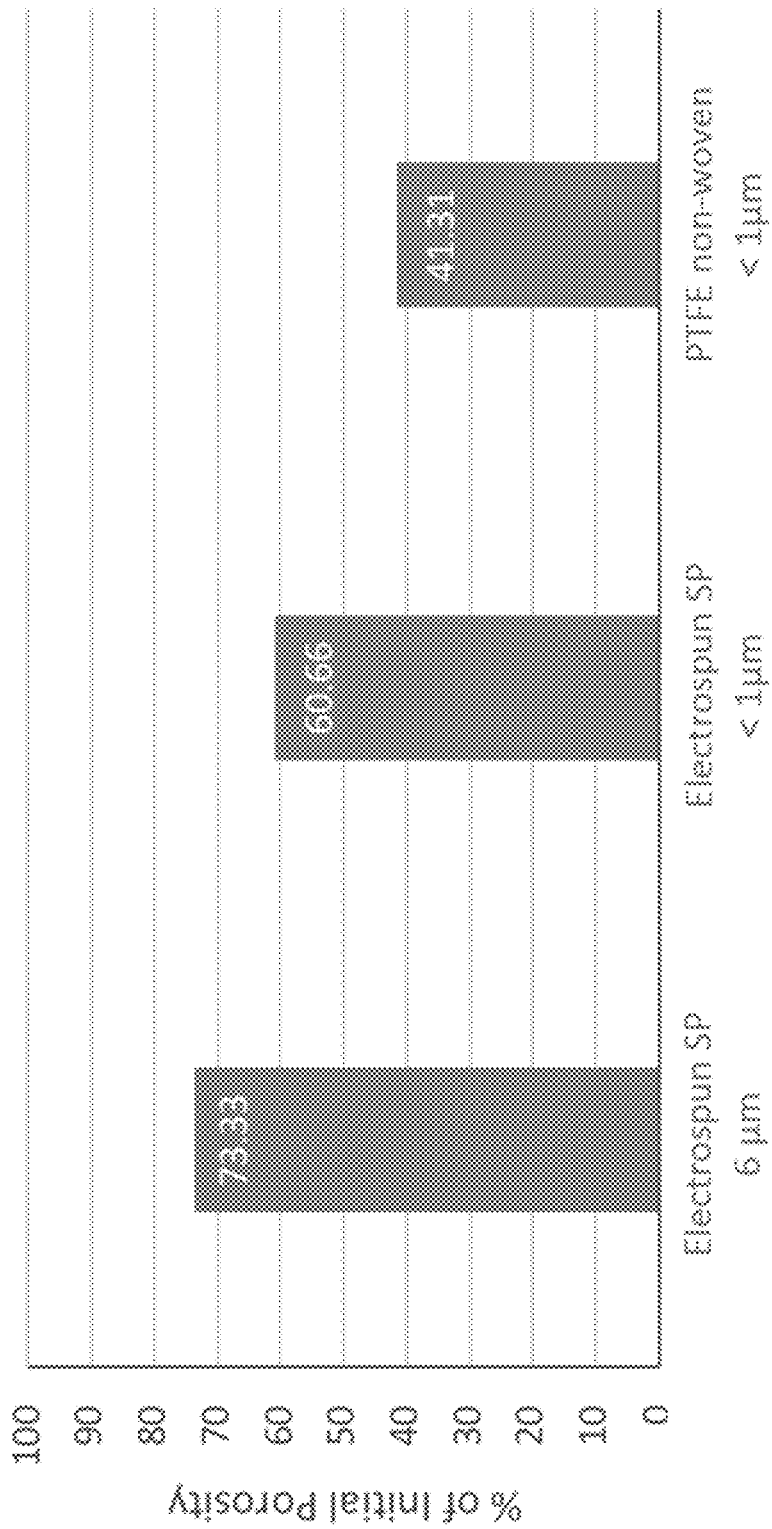
FIG. 4 shows according to an exemplary embodiment of the invention the porosity decrease observed under SEM for test materials post blood perfusion due to platelet aggregation/spreading, expressed as a percentage of initial porosity

Quantification of the surface coverage of blood products on the test materials was based on analysis of decrease in total porosity of surfaces observed under SEM. Analysis was carried out using ImageJ software, the stages of which are outlined in FIGS. 3A-C. In brief, the SEM image is prepared via cropping and contrast enhancement and conversion to a binary image (containing only black or white pixels". This binary image is then analysed via ImageJ's "Threshold" feature, which counts the total number of black pixels within the image. This process is conducted on three characteristic SEM images of the sample surface before blood perfusion, and SEM images of the surface after blood perfusion and the change in porosity is reported. FIG. 4 shows the decrease in porosity due to surface coverage by blood products for all material samples after perfusion over surface.

In addition to blood-flow experiments using thrombin-deactivated human blood, static experiments were performed using whole blood. In these experiments, blood from healthy donors was placed into 96-well plates along with a sample of test material. Sample chambers were incubated for 20 minutes at 37 degrees Celsius on a shaking incubator before blood was removed via pipette and characterized via flow cytometry.

Figure 5:
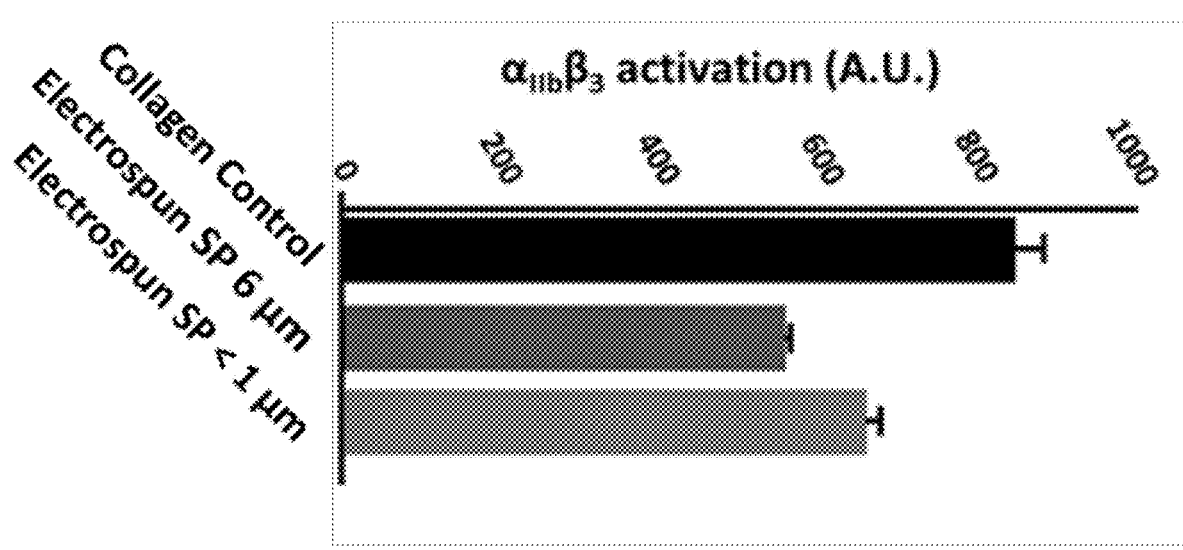
FIG. 5 shows according to an exemplary embodiment of the invention detection of activated $\alpha_{IIb}\beta_3$ in perfused blood from test surfaces.

These experiments showed an unexpected reduction of up to 50% of cell adhesion for glycoprotein $\alpha_{IIb}\beta_3$ in blood incubated with electrospun SP material as compared in the effused blood samples from non-woven PTFE, a reduction not observed for another adhesion glycoprotein, P-selectin (FIG. 5).

Highly Effective Inhibition of Platelet Adherence to Fibers of Supramolecular Polymer by Inactivation of Integrin $\alpha_{IIb}\beta_3$ Based on results arising from cytometry of whole-blood experiments on various samples, platelet activation by and adherence to electrospun SP fibers was hypothesised to be strongly and specifically dependent on the integrin, $\alpha_{IIb}\beta_3$.

Figure 6:
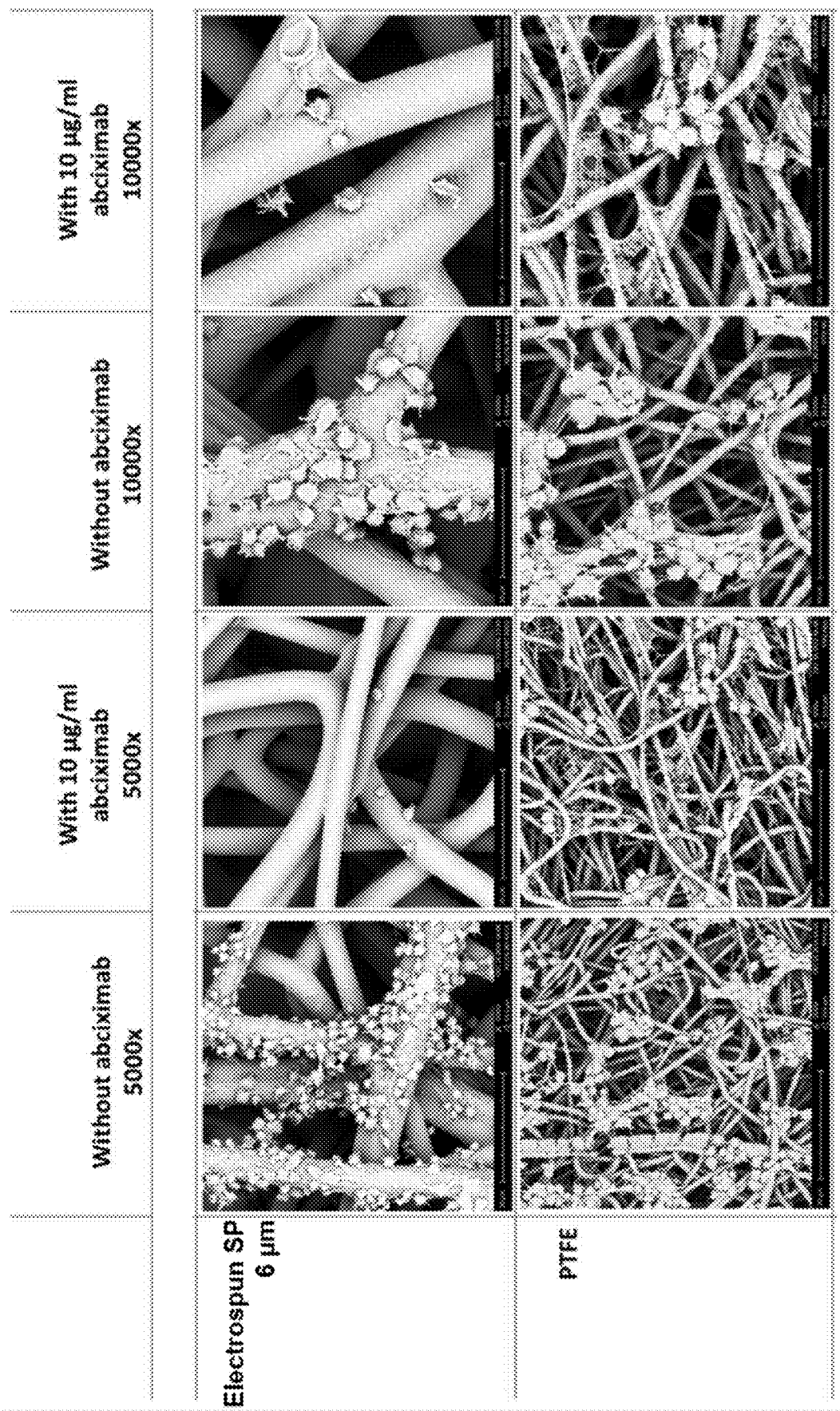
FIG. 6 shows according to an exemplary embodiment of the invention SEM images at various magnifications of platelet adherence to electrospun SP material and PTFE non-woven materials with and without the addition of abciximab.

To confirm the mechanism of adherence, the drug Abciximab (ReoPro) an inhibitor of $\alpha_{IIb}\beta_3$, was added to healthy citrated blood at a clinically relevant dosage of 10 µg/ml. Blood was subsequently perfused over a sample material of electrospun non-woven SP material with fiber diameter of 4-6 µm using a controlled shear rate flow cell for 30 minutes as well as a sample of non-woven PTFE. Post-flow, the sample was fixed and imaged using Scanning Electron Microscopy, allowing direct visualization of platelet adherence. The addition of Abciximab (ReoPro) resulted in greatly decreased platelet adhesion as compared to control (FIG. 6). Further, the effect was greatly exaggerated as compared to PTFE nonwoven fibrous material. The ability to almost totally inhibit platelet adhesion to a synthetic polymer material (XP) with a single clinically available medication (ReoPro) at physiologically relevant dosages is believed to be a novel finding, with applications in a range of blood contact applications.

The number of absorbed platelets to test materials counted from SEM images above showed a reduction of 97% for SP electrospun material (226 to 6) after addition of abciximab, compared to 78% (236 to 51) on PTFE non-woven. Based on the apparent specific efficacy of Abciximab as a platelet absorption inhibitor for electrospun SP materials, as well as data presented above on glycoprotein IIb/IIIa levels post-perfusion, in vitro thrombogenicity testing, it is proposed that any antiplatelet chemotherapeutic agent with a mechanism of action targeting the inhibition of glycoprotein IIb/IIIa will have a similarly exaggerated effect on SP electrospun materials. The mechanism for this exaggerated effect is unclear, and is hypothesized to be driven by a dissimilarity in apparent surface charge density and/or associated hydrophobicity of SP electrospun material. The surface charge density, or the electric charge possessed per unit area of material surface is known to effect the binding of proteins. This effect arises due to the charge distribution within these proteins leading to an attraction/repulsion effect from disparately/similarly charged surfaces, respectively. Furthermore, materials showing a significant degree of surface roughness are likely to further exaggerate or compound this effect, as the total charge density increases at areas of curvature such as microscale protrusions from a flat surface as well as nano-scale roughness of these surfaces and protrusions. Such an effect of surface charge on platelet activation is established in the literature for dendritic synthetic polymers (Dobrovolskaia et al, 2012 Nanoparticle size and surface charge determine effects of PAMAM dendrimers on human platelets in vitro. Molecular pharmaceutics. 2012; 9(3):382-393. doi:10.1021/mp200463e).

Further, the inclusion of chemotherapeutic agents, such as abciximab, in electrospun fibres and polymer coatings is known (US20100280594). Due to the apparent specific interaction between SP electrospun materials and glycoprotein IIb/IIIa inhibitors, particularly abciximab, a highly effective antithrombotic effect may be realized through this method. The combination of bioabsorbable electrospun supramolecular constructs with abciximab or other compounds targeting glycoprotein IIb/IIIa inhibition is expected to be especially beneficial because the combination may allow the regeneration of body own tissue in applications such as coronary bypass grafts, for which this was not possible before. It is envisioned that other methods of inclusion of such chemotherapeutics, including but not limited to incorporation into the electrospun fiber material, either covalently or else, absorbed at the fiber surface or included in a carrier material coated onto the non-woven surface is possible as well. Yet another possibility would be to administer said chemotherapeutics, either orally, intravenously or otherwise. This could be done before, during or after the implantation of the cardiovascular graft.

Role of Platelets in Thrombotic Occlusion of Small Diameter Grafts of Electrospun Supramolecular Polymer (SP) Material in Large Animal Models To demonstrate the role of platelets in thrombotic occlusion of small diameter grafts of electrospun SP material in vivo, 4 mm grafts were implanted as coronary bypass graft in an ovine model with varying medication strategies aimed at platelet inhibition. The combination of relatively low flow rates (generally <120 mL/min), curved graft paths, and small diameters are expected to present a worst-case scenario for synthetic grafts, allowing the efficacy of anti-platelet treatments in-vivo to be critically assessed.

Figure 7A:
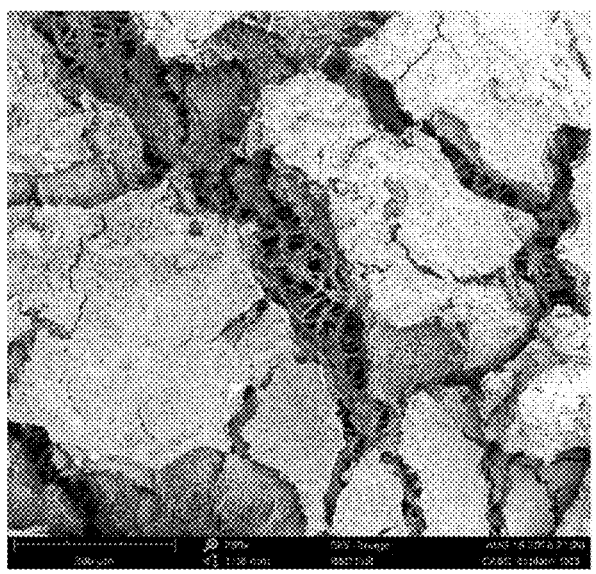
FIGS. 7A-C show according to an exemplary embodiment of the invention SEM images (250×) magnification of explanted samples from animals medicated with, FIG. 7A) Heparin FIG. 7B) Heparin & Aspirin, and FIG. 7C) Heparin, Aspirin & Plavix.
Figure 7B:
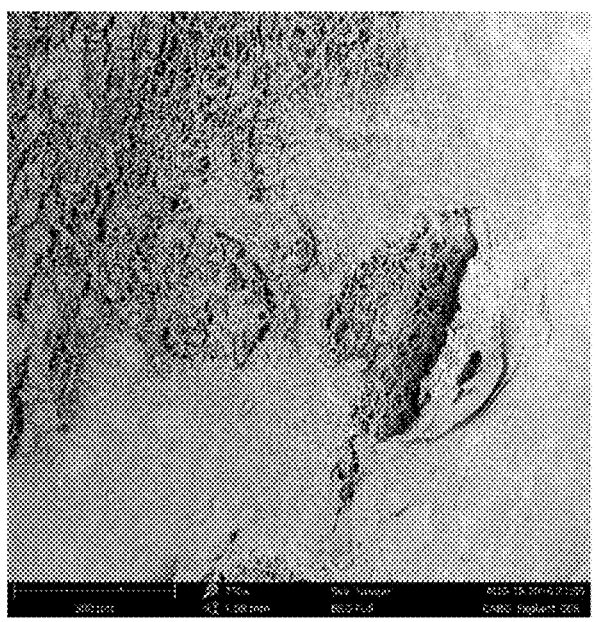
Figure 7C:
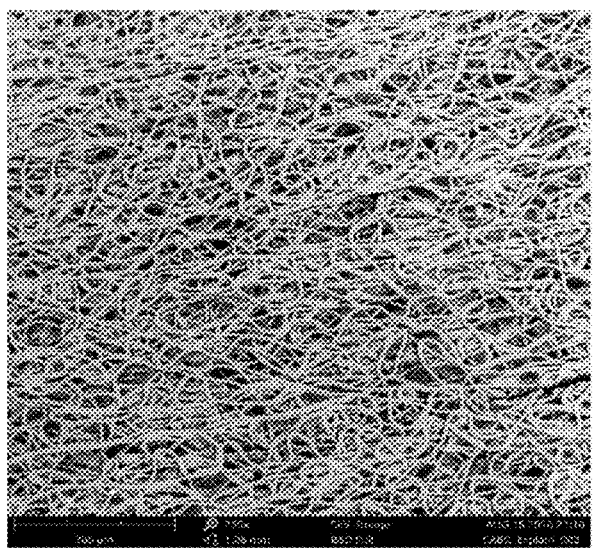

Prior to surgery, animals were medicated using combinations of Heparin, Heparin-Aspirin and Heparin-Aspirin-Plavix. As heparin is a well-established inhibitor of the thrombin-driven coagulation pathway, all observed coagulation response can be considered platelet-driven. Aspirin and Plavix both act on secondary platelet activation, that is the ability of activated platelets to activate further circulating platelets, with Plavix being a more powerful agent. Grafts were implanted for 4 hours before explantation, fixing and characterization via histology and SEM. As can be seen in FIG. 7 the use of increasing platelet-inhibition therapy resulted in significant reduction in thrombus formation on the nonwoven surface of the graft. These results indicate that platelet activation and aggregation are the predominant mechanisms of thrombogenesis in vivo.

Long Term Thrombotic Response of Small Diameter Grafts of SP Electrospun Material in Large Animal Models To demonstrate the long term thrombogenic response of small diameter grafts comprising SP electrospun materials, 6 and 7 mm grafts were implanted as carotid artery interpositions in an ovine model (n=4 and n=2, respectively). Graft patency was evaluated immediately after implant via angiography and sonogram, and subsequently via sonogram at day 0, 7, 14, 21 and 28, and once per month thereafter. Proximal, distal and mid sections of grafts were evaluated for lumen diameter changes over this time. Half of the test animals were sacrificed and the grafts explanted at the 6 month time point for gross histological characterization, with the remaining animals planned for sacrifice and explanation at 12 months.

Animals were medicated beginning at time of surgery with 0.4 mL "Lovenox®" Enoxaparin (low molecular weight heparin) twice per day for 90 days, as well as with 125 mg aspirin once per day until sacrifice.

Figure 8A:
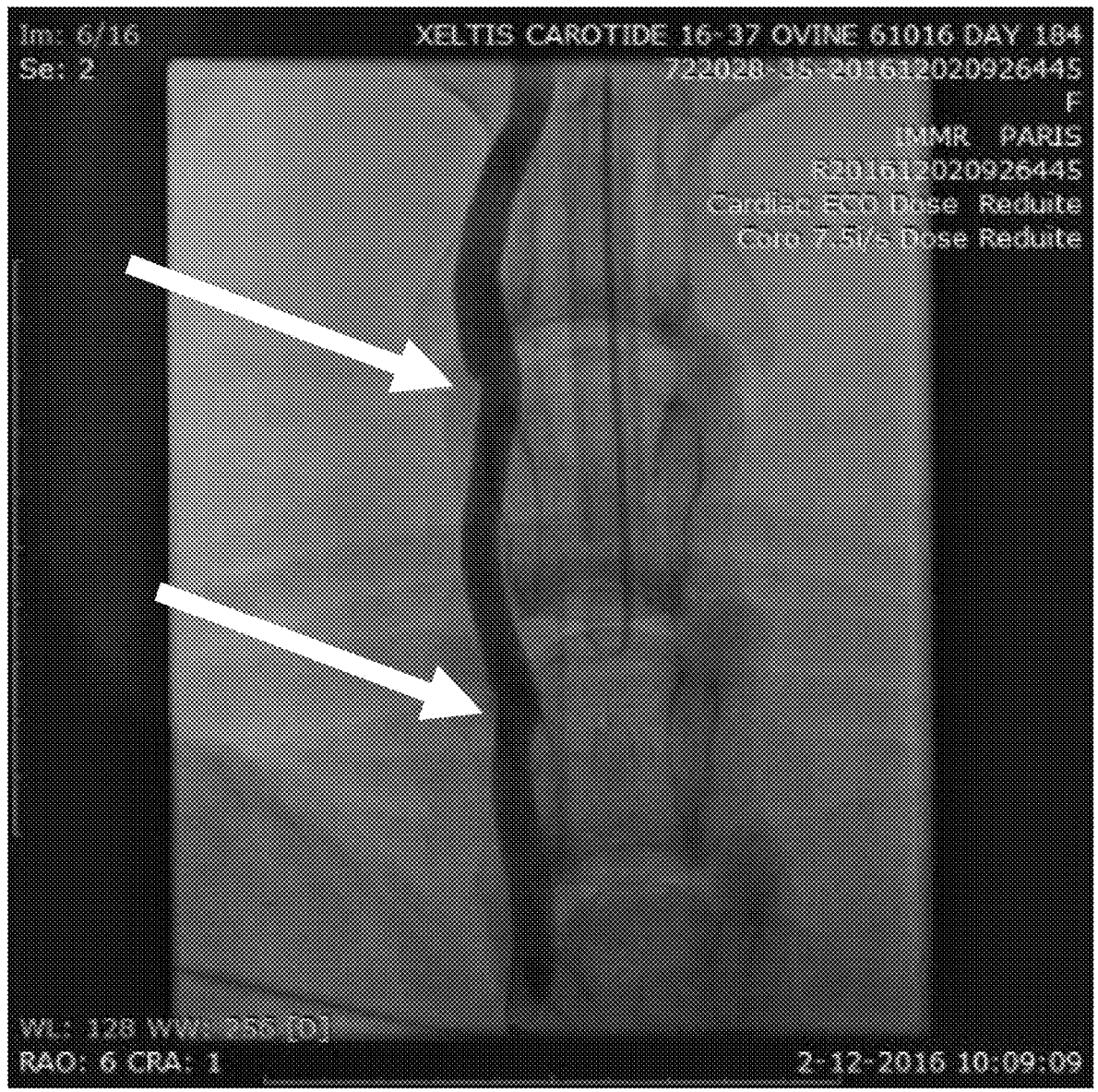
FIGS. 8A-C show according to an exemplary embodiment of the invention angiography of 6 mm (FIGS. 8A-B) and 7 mm (FIG. 8C) carotid interposition grafts after 6 months implantation, arrows indicate Distal (top) and Proximal (bottom) anastomoses.
Figure 8B:
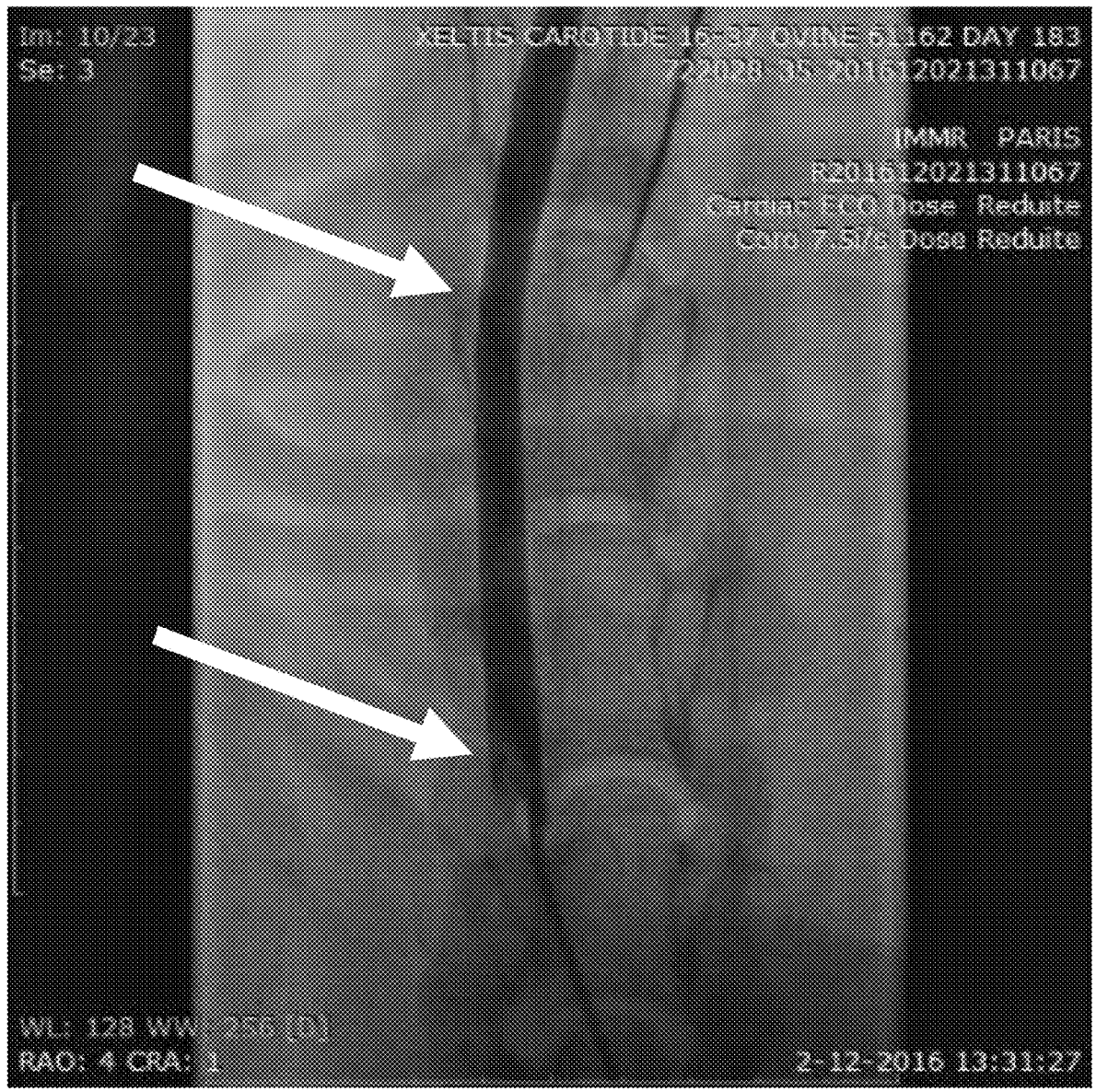
Figure 8C:
Figure 9:
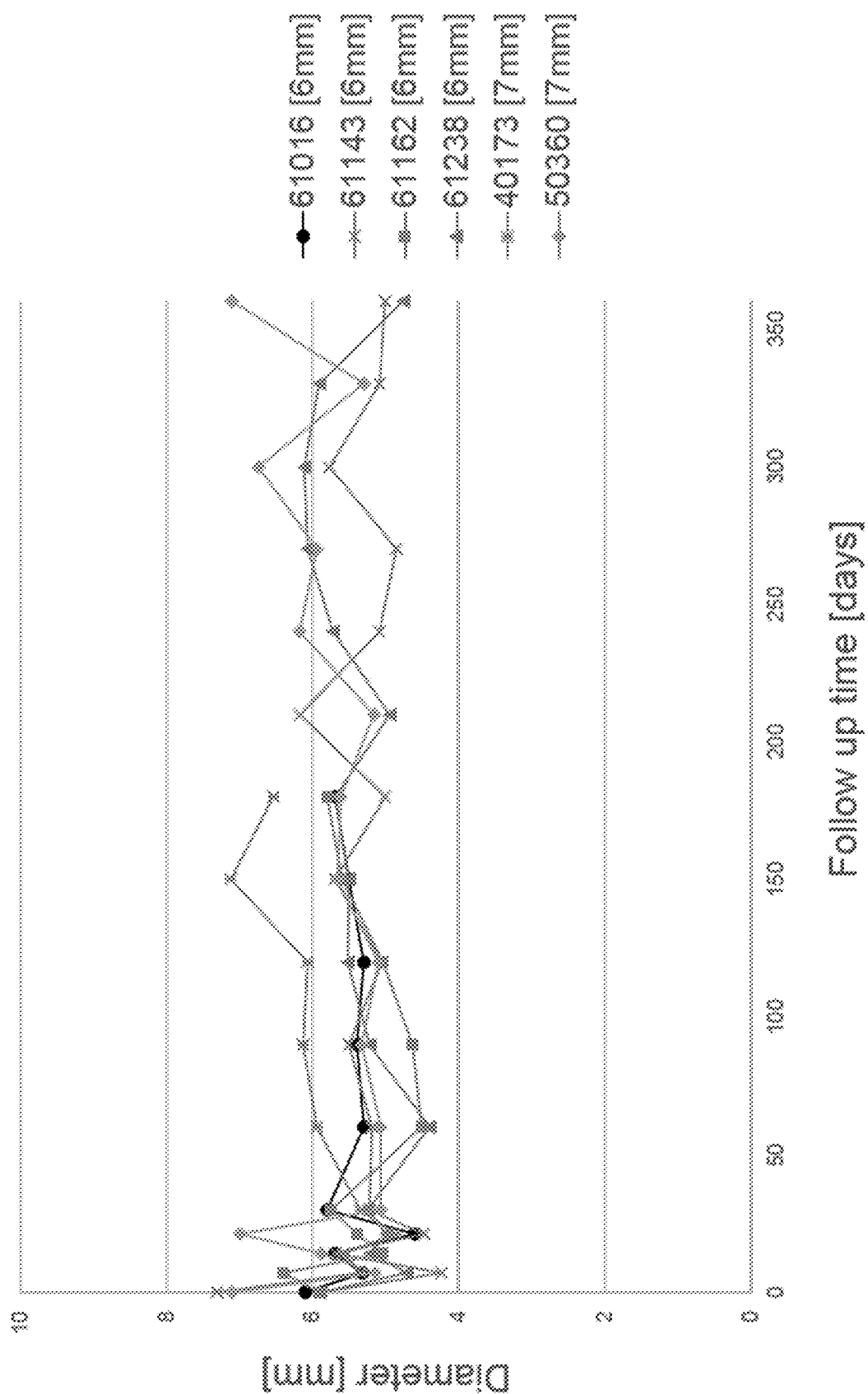
FIG. 9 shows according to an exemplary embodiment of the invention internal diameter of graft, measured immediately prior to distal anastomosis, for 6 and 7 mm carotid interposition grafts over 36 weeks.
Figure 10:
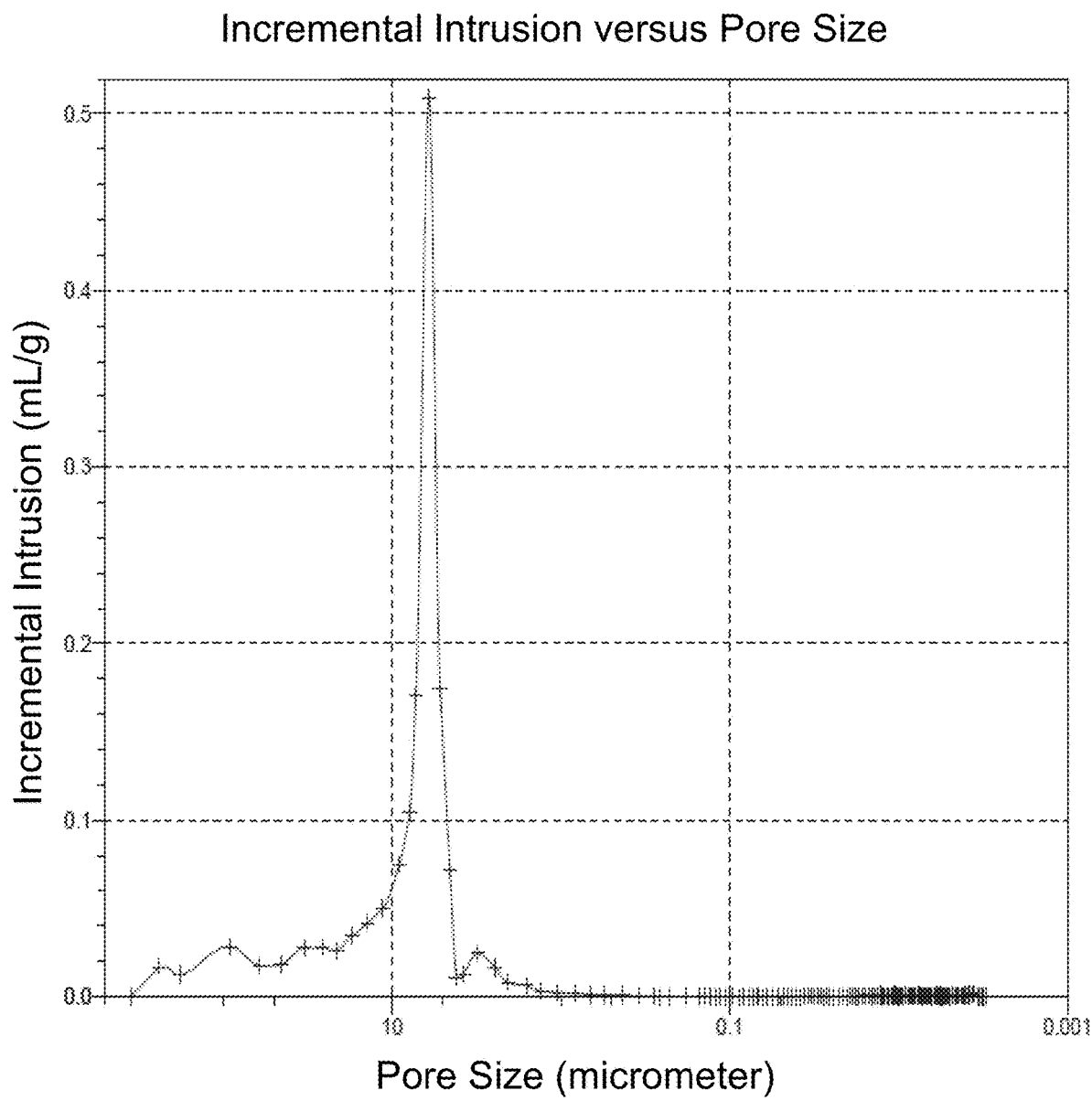
FIG. 10 shows according to an exemplary embodiment of the invention data of incremental infusion versus pore size on a small diameter graft, showing that most of the pores range between 5 and 10 micrometers in size. The average pore size for cardiovascular grafts according to this invention is different than observed or desired for pulmonary valves.

As can be seen in FIG. 8, angiography showed good patency of grafts prior to explantation at 6 month time point. FIG. 9 shows the diameter of the distal anastomosis (most prone to thrombotic occlusion) over the course of the study to data.

Method of Making a Supramolecular Polymer

In one exemplary embodiment, a supramolecular polymer could be made using one of the recipes described in U.S. Provisional Application 62/611,431 filed on Dec. 28, 2017 which is herein included by reference for all that it teaches and to which this application claims priority.

According to these recipes, supramolecular compounds are defined as hard-blocks covalently bonded with soft-blocks. The hard blocks are based on UPy moieties. The soft block is the backbone of the supramolecular compounds. Polycarbonate (PC) was used as it showed surprisingly benefit for the purposes and objectives of this invention, especially compared to polycaprolactone.

The ratio between the soft block and the hard block has an influence on the material properties. Herein, we describe that ratios of components within the hard block section has a tremendous impact on properties such as durability. We describe here a specific combination of ratios within the hard block and length of the polymer used to form soft block that lead to enhanced mechanical properties (durability). Specifically, polycarbonate with a molecular weight range of 500-2000 Da provide enhanced durability and reduced fatigue compared to e.g. polycaprolactone. The hard block is composed of the Upy component, a diisocyanate and a chain extender. The ratio (R) within the hard-blocks for 2-ureido-4[1H]-pyrimidinone (UPy) compounds and chain extenders at a range of 1.5 to 3 for the chain extenders over the UPy compounds.

Synthesis of Supramolecular Polymers

PCL Polymer—XP1

Telechelic hydroxy terminated polycaprolactone with a molecular weight of 800 g/mol (30.0 g, 37.5 mmol, dried under vacuum), 1,6-hexanediol (4.4 g, 37 mmol), and UPy-monomer (6.3 g, 37 mmol) were dissolved in dry DMSO (105 mL) at 80° C. To this reaction mixture was added hexamethylene diisocyanate (18.8 g, 111.5 mmol) while stirring, followed by the addition of one drop of tin dioctoate. This reaction mixture was stirred overnight at 80° C. The next day, the reaction mixture was cooled to 25° C. and its viscosity was lowered by the addition of additional DMSO in order to precipitate the mixture in water. The polymer was collected as white elastic solid, redissolved in chloroform/methanol (7/3 v/v) and reprecipitated in an excess methanol. This resulted in a clear elastic solid after drying under vacuum at 50° C. SEC (THF, PS-standards): Mn=13 kg/mol, D=1.6. See also WO2014185779.

PC Polymer

Polymers made with polycarbonates with molecular weight varying from 500 to 3000 g/mol were synthesized in a similar manner as for XP1. The changes were made depending on the length of the polycarbonate and the desired ratio between the components. Molar ratio can be expressed as followed. A (polycarbonate) is fixed at 1. B (chain extender) varies between 0 and 3, D (Upy) from 0.3 to 2 and and C is always equal to 0.8 to 1.2 times the total molar amount of A plus B plus D. Molar ratio B/D is noted R. Table 1 provides a non-exhaustive list of examples of supramolecular polymers obtained according aforementioned instructions.

TABLE 1

List of material

| Material | Soft block | Ratio R |
|---|---|---|
| XP1 | PCL 800 | 1 |
| XP2 | PCL 800 | 2 |
| XP3 | PC 2000 | 2 |

Figure 11:
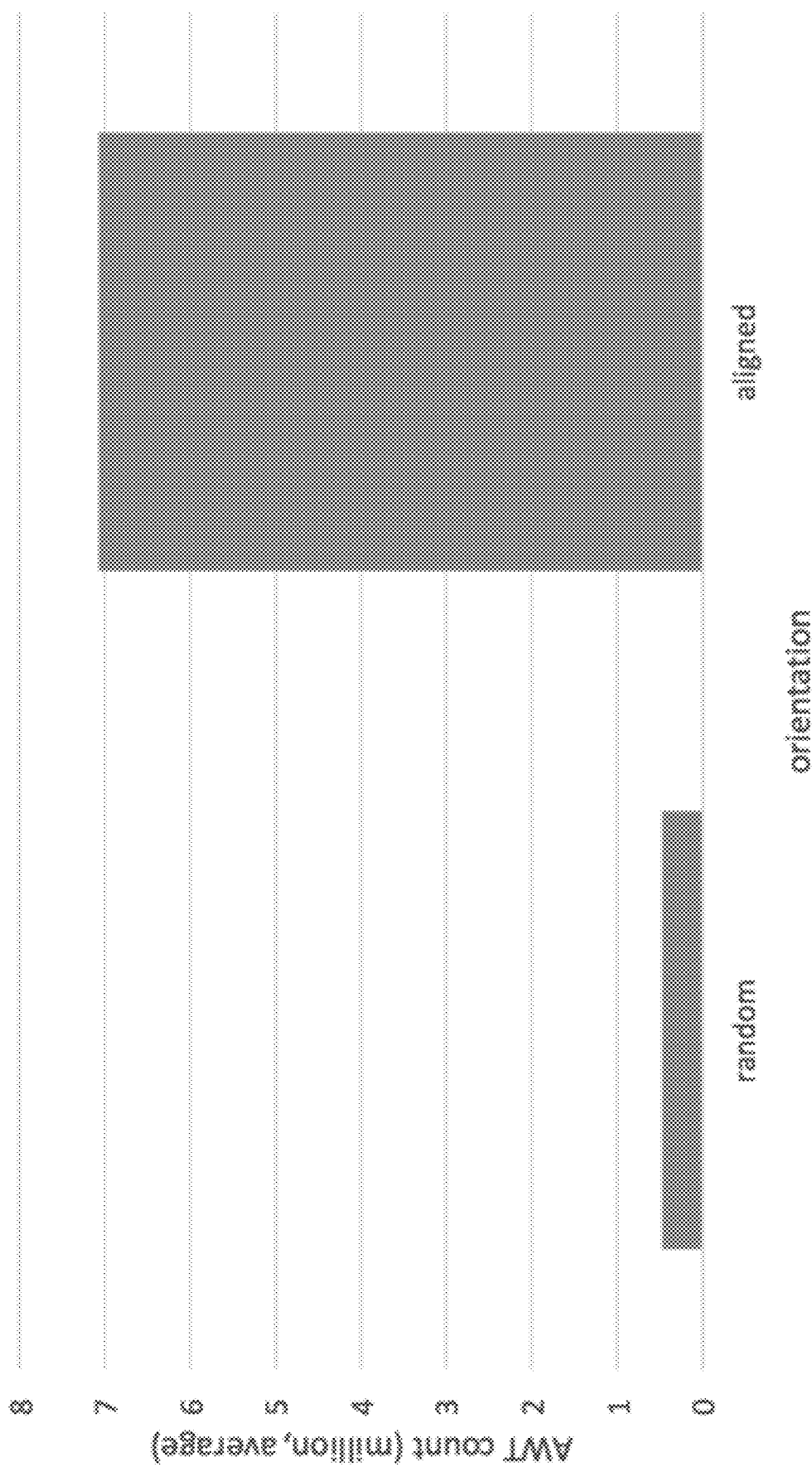
FIG. 11 shows according to an exemplary embodiment of that alignment of fibers enables the increase in fatigue resistance, expressed as the number of cycles until failure in an Accelerated Wear Tester (AWT) for a supramolecular polymer valve under aortic conditions according to ISO 5840.

A feature that can for example influence durability is the alignment of the fibers within the scaffold. The preferred fiber alignment is circumferential around an imaginary axis of the implant wherein the axis points in the direction of blood flow in case of a tubular implant. We can clearly see that alignment enables the increase in fatigue resistance from FIG. 11. Alignment, defined as the linear elastic stiffness ratio between the preferred fiber direction and perpendicular to the preferred fiber direction was varied up to 8:1. While the example of FIG. 11 is based on the comparison of alignment in an electrospun supramolecular polymer heart valve, it is anticipated that the same principle will apply to cardiovascular grafts.

Complementary Information

1. Ranges (Durability Focus)

The ratio R was varied from 0 to 3. Enhanced/best fatigue resistance behavior was obtained for ratio above 1.5.

PC length was varied from 500 to 3000 g/mol. Enhanced/best fatigue resistance behavior was obtained for PC length of 1000.

Chain extender mass ratio was varied from 0 to 15. Enhanced/best fatigue resistance behavior was obtained for higher ratio (above 9 weight percent (wt %)).

2. Scaffold Structure

Thickness can be varied between from a few μm to mm, but preferred thickness is between 200 and 800 μm and even preferable between 250 and 550 (average at 300 and 500 provide good results).

Fiber diameters can be obtained in a big range from 1 μm to 20 μm. Preferably, we work in 3-15 μm range and even more preferably in the 4-10 μm range.

Alignment of fibers is another parameter that enhances durability especially when the electrospinning is not guided resulting in a random distribution to a 1:2 (Circumferential:Axial) organization (meaning stiffness in the axial direction is twice the one in the circumferential direction). The fibers can be aligned with a ratio from infinity:1 to 1:2. It is preferable to work with a ratio between 2:1 to 8:1 as they provide good improvement in durability.

Pore size: the matrix material comprises pores having a diameter ranging from 1-300 micrometer and preferably ranging from 5-100 micrometer.

Porosity: the matrix material comprises a fibrous network and has a porosity of between 50% and 80%.

Method of Making the Cardiovascular Graft

In one exemplary embodiment to make the cardiovascular graft, a supramolecular polymer (SP) material, for example obtained as in one of the recipes infra, is dissolved to a concentration of 11.5 wt % in a solvent mixture of chloroform and hexafluoroisopropanol. This solution is delivered via syringe pump to a blunt-ended stainless steel needle maintained at an electric voltage of between 5 and 10 kilovolts, resulting in an electrostatically-driven whipping jet. This jet is attracted to a cylindrical collector charged to a negative voltage of between 1 and 4 kilovolts, resulting in the formation of a highly porous, fibrous non-woven coating. After a thickness of 0.5 mm of electrospun polymer material is deposited, removal from the collector device is achieved via separation with a soft-tipped spatula, resulting in an electrospun tubular graft with wall thickness of 0.5 mm.

Conclusion

The data described herein demonstrates an unexpected effect of the cardiovascular graft of this invention on the activation, adherence and spreading of platelets. A quantifiable reduction in platelet-driven thrombus formation on cardiovascular graft as compared to known biocompatible synthetic polymers (e.g. FIG. 4: porosity reduction of 27% for electrospun SP materials and 59% for PTFE) is demonstrated. In addition, the previously unknown and unexpected dependence on a singular cell-adhesion protein glycoprotein IIb/IIIa is presented. The basis for this unexpected interaction is hypothesised to be a result of the surface charge of electrospun fibres of SP. This dependence of platelet adhesion on a particular glycoprotein allows platelet driven thrombosis to be strongly influenced by a single chemotherapeutic agent, in contrast with known biocompatible synthetic polymers such as PTFE, which require a broader spectrum of inhibition to cell adhesion molecules. The incorporation or surface absorption of such chemotherapeutics with electrospun fibres of SP material to provide site-specific and highly effective platelet inhibition is proposed pending further investigation.

What is claimed is:

1. A method of using a cardiovascular graft to reduce platelet adhesion, comprising:
   having a cardiovascular graft designed as a tubular structure with an inner wall made out of a fibrous network of supramolecular compounds having hard-blocks covalently bonded with soft-blocks, wherein the hard-blocks comprise 2-ureido-4[1H]-pyrimidinone (UPy) compounds, wherein the fibrous network is a bioresorbable electrospun non-woven fibrous network with fibers having an average fiber diameter of 1-10 microns, and wherein the tubular structure has an inner diameter between 2-8 mm, and an inner wall thickness of 20-900 micrometers, wherein the soft-blocks comprise a polyurethane, polycarbonate, poly(ortho)ester, polyphosphoester, polyanhydride, polyphosphazene, polyhydroxyalkanoate, polyvinylalcohol, polypropylenefumarate or any combination thereof; and
   using the cardiovascular graft to reduce platelet adhesion upon implantation of the cardiovascular graft in a human body.

2. The method as set forth in claim 1, further comprises administering an $\alpha_{IIb}\beta_3$ inhibitor in combination with the implantation of the cardiovascular graft.

3. The method as set forth in claim 1, wherein the inner wall has a thickness of 200 micrometers to 900 micrometers and has pores with an average pore size between 5 and 10 micrometers.

4. The method as set forth in claim 1, wherein the inner wall has pores with an average pore size between 5 and 8 micrometers and an average porosity ranging from 50 to 80%.

5. The method as set forth in claim 1, wherein the tubular structure has an inner diameter between 3-6 mm and a wall thickness of 200-800 microns.

6. The method as set forth in claim 1, wherein the tubular structure has an inner diameter between 4-8 mm and an inner wall thickness of 300-900 microns.

7. The method as set forth in claim 1, wherein the fibers having an average fiber diameter of 4-8 microns.

8. The method as set forth in claim 1, wherein the fibers having an average fiber diameter of 4-6 microns.

9. The method as set forth in claim 1, wherein the molecular weight of the soft-block ranges between 500 and 3000 Da.

10. The method as set forth in claim 1, wherein the hard-blocks further comprise chain extenders at a range of 1 to 5 for the chain extenders over the UPy compounds.

11. The method as set forth in claim 1, wherein the hard-blocks further comprise chain extenders at a range of 1.5 to 3 for the chain extenders over the UPy compounds.

12. The method as set forth in claim 1, wherein the inner wall of the graft is hydrophobic, with a water contact angle of between 110 and 140 degrees.

13. The method as set forth in claim 1, wherein the tubular structure has an outer wall reinforced by a braided structure, polymer strands, compounds or a combination thereof to provide resistance to prevent collapse of the cardiovascular graft.

* * * * *